United States Patent
Floeder et al.

(10) Patent No.: US 7,937,233 B2
(45) Date of Patent: May 3, 2011

(54) PREFERENTIAL DEFECT MARKING ON A WEB

(75) Inventors: Steven P. Floeder, Shoreview, MN (US); James A. Masterman, Lake Elmo, MN (US); Carl J. Skeps, Lakeville, MN (US); Jason P. Smith, Saint Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 455 days.

(21) Appl. No.: 12/104,700

(22) Filed: Apr. 17, 2008

(65) Prior Publication Data

US 2009/0265127 A1 Oct. 22, 2009

(51) Int. Cl.
*G06F 19/00* (2011.01)
*G06K 9/00* (2006.01)

(52) U.S. Cl. .............. 702/81; 700/122; 382/141
(58) Field of Classification Search ............ 702/35, 702/81, 82; 382/141, 143, 149; 700/10, 700/122, 124; 707/104.1
See application file for complete search history.

(56) References Cited

U.S. PATENT DOCUMENTS

| 4,134,684 A | 1/1979 | Jette |
| 4,982,600 A | 1/1991 | Kiso et al. |
| 5,099,504 A | 3/1992 | Pettit |
| 5,467,194 A | 11/1995 | Pellinen et al. |
| 6,665,432 B1 | 12/2003 | Evans et al. |
| 7,027,934 B2 | 4/2006 | Skeps et al. |
| 7,120,515 B2 | 10/2006 | Floeder et al. |
| 2005/0141760 A1* | 6/2005 | Floeder et al. ............ 382/141 |
| 2005/0232475 A1 | 10/2005 | Floeder et al. |

FOREIGN PATENT DOCUMENTS

EP 0 516 913 A2 12/1992

OTHER PUBLICATIONS

Floeder et al, U.S. Appl. No. 11/828,369, filed Jul. 26, 2007; Titled: "Multi-Unit Process Spatial Synchronization".
Floeder et al, U.S. Appl. No. 11/828,376, filed Jul. 26, 2007, Titled: "Fiducial Marking for Multi-Unit Process Spatial Synchronization".

* cited by examiner

*Primary Examiner* — Bryan Bui
(74) *Attorney, Agent, or Firm* — Steven A. Bern

(57) ABSTRACT

A system for preferentially marking defects on a web is described. The system includes a web of material to be converted into individual sheets of a plurality of different grade levels, a database storing anomaly data of anomalies on the web, wherein an anomaly is a potential defect in at least one of the plurality of different grade levels, a marker that associates a unique mark with at least one of the grade levels, and a controller to retrieve the anomaly data from the database and to signal the marker as to where to make a mark, wherein the marker applies the mark associated with at least one of the grade levels for which the anomaly may cause a defect. The system may provide advantages, such as that a converter of various products from a single web roll may determine which regions of the web satisfy each grade level.

27 Claims, 13 Drawing Sheets

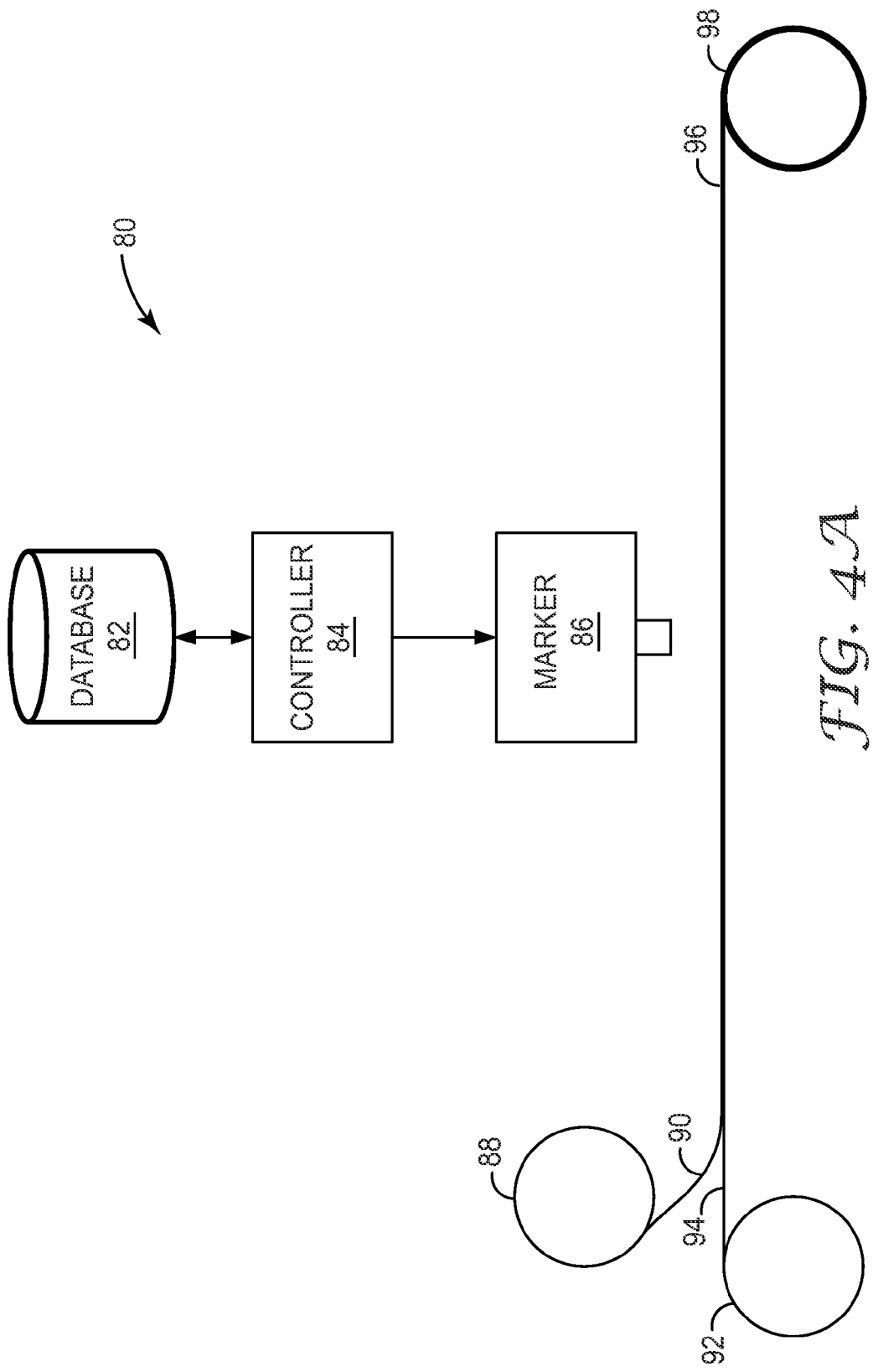

PREFERENTIAL DEFECT MARKING ON A WEB

TECHNICAL FIELD

The invention relates to automated inspection systems, and more particularly, to inspection of continuously moving webs.

BACKGROUND

Inspection systems for the analysis of moving web materials can be important in the manufacture of paper, non-woven materials, and polymeric films, as well as metal fabrication. These inspection systems can be used for both product certification and online process monitoring. However, with webs of commercially viable width, the web speeds that are typically used, and the pixel resolution that is typically needed in these manufacturing operations, data acquisition speeds of tens or even hundreds of megabytes per second are required, and it is a continual challenge to process images and to perform accurate defect detection at these data rates.

In addition, web process manufacturing operations can require multiple unit operations be performed on a single roll of material during its production. For example, certain complex web-based products, such as flexible circuits, may require as many as fifteen distinct manufacturing operations over the course of days or even weeks, often utilizing multiple production lines at different physical sites. In these circumstances, it is typical to collect the web into a roll after each process and ship the roll to a different location where it is then unrolled, processed, and again collected onto a different roll. Each process step may introduce new anomalies into a web, which may or may not cause the web to be defective when it is analyzed during a subsequent process step. Moreover, subsequent process steps can make it more difficult, if not impossible, to detect anomalies occurring in earlier process steps.

SUMMARY

In general, this application describes techniques for the automated inspection of moving webs. More specifically, the techniques described herein may be used to automatically inspect a moving web for anomalies, taking into account the various products into which the web may be converted. For example, an anomaly may cause a defect in one product, yet be harmless in another product. An inspecting system may identify an anomaly on a web during inspection and determine whether the anomaly would cause a defect in each of the potential products into which the web may be assembled after conversion into individual sheets. The inspection system may associate a unique mark with each product into which the individual web sheets may be assembled. The inspection system may place a mark on the web or on a cover sheet over the web at the position of each anomaly to indicate each product for which the anomaly may cause a defect.

In one embodiment, the invention is directed to a method for preferentially marking the locations of anomalies or defects on a web. Steps in the method include obtaining a web to be converted into individual sheets of a plurality of different grade levels, associating a unique mark with each of the different grade levels, obtaining anomaly data that identifies positions of anomalies on the web for each of the grade levels, wherein each of the anomalies represents a physical deviation of the web that is a potential defect for at least one of the plurality of different grade levels, and marking the position of each anomaly on the web at the position of the anomaly, wherein each anomaly is marked with each of the marks corresponding to each of the grade levels for which the anomaly is determined to be a defect.

In another embodiment, the invention is directed to a method including the steps of receiving a web to be converted into individual sheets of a plurality of different grade levels, wherein the web has marks to indicate positions of anomalies on the web, wherein the marks include a unique mark for each of the different grade levels, separating the web into the individual sheets, selecting, for each individual sheet, one or more of the products into which to incorporate the sheet in accordance with the marks, and incorporating each sheet into the selected product or products.

In another embodiment, the invention is directed to a system that includes a web of material to be converted into individual sheets of a plurality of different grade levels, a database storing anomaly data of anomalies on the web, wherein an anomaly is a potential defect in at least one of the plurality of different grade levels, a marker that associates a unique mark with at least one of the grade levels, and a controller to retrieve the anomaly data from the database and to signal the marker as to where to make a mark, wherein the marker applies the mark associated with at least one of the grade levels for which the anomaly may cause a defect.

In another embodiment, the invention is directed to a computer-readable medium containing instructions. The instructions cause a programmable processor to retrieve web identifying information, wherein the web is to be converted into individual sheets of a plurality of different grade levels, associate a unique mark with each of the grade levels; obtain anomaly data that identifies positions of anomalies on the web for each of the grade levels, wherein each of the anomalies represents a physical deviation of the web that is a potential defect for at least one of the plurality of different grade levels, and signal a marker to mark the position of each anomaly on the web at the position of the anomaly, wherein each anomaly is marked with each of the marks corresponding to each of the grade levels for which the anomaly is determined to be a defect.

The techniques described herein may provide several advantages. For example, a converter of various products from a single web roll may determine which regions of the web roll may be most suited for use in conversion to sheets for incorporation into each product. As another example, a producer may use the anomaly data when determining a price for the web roll for sale to a converter. That is, a web roll with fewer anomalies may carry a higher price than a web roll with relatively more anomalies.

Along with the roll, the producer may distribute the data and markings to a converter, so the converter does not need to re-inspect the roll for anomalous regions. The producer may save costs since it may not be necessary to separate and discard anomalous regions, while the converter may be able to purchase the web roll and data set at a discount over an anomaly-free web roll. Moreover, the converter may be able to utilize regions with certain anomalies, which might otherwise be discarded, for a product in which the anomaly will not cause a defect, thus salvaging what would otherwise be wasted material.

The details of one or more embodiments of the invention are set forth in the accompanying drawings and the description below. Other features, objects, and advantages of the invention will be apparent from the description and drawings, and from the claims.

DEFINITIONS

For purposes of the present invention, the following terms used in this application are defined as follows:

"web" means a sheet of material having a fixed dimension in one direction and either a predetermined or indeterminate length in the orthogonal direction;

"sequential" means that an image is formed by a succession of single lines, or areas of the web that optically map to a single row of sensor elements (pixels);

"pixel" means a picture element represented by one or more digital values;

"defect" means an undesirable occurrence in a product;

"anomaly" or "anomalies" mean a physical deviation of the web from normal product that may or may not be a defect, depending on its characteristics and severity;

"filter" is a mathematical transformation of an input image to a desired output image, filters are typically used to enhance contrast of a desired property within an image;

"application-specific" means defining requirements, e.g., grade levels, based on the intended use for the web;

"products" are the end products that incorporate individual sheets (also referred to as components) produced from a web, e.g., a rectangular sheet of film for a cell phone display or a television screen; and "conversion" is the process of physically cutting individual sheets from a web that may be subsequently assembled into products.

BRIEF DESCRIPTION OF DRAWINGS

FIGS. 4A-4C are block diagrams illustrating exemplary embodiments of web marking systems according to the techniques described herein.

DETAILED DESCRIPTION

Figure 1:
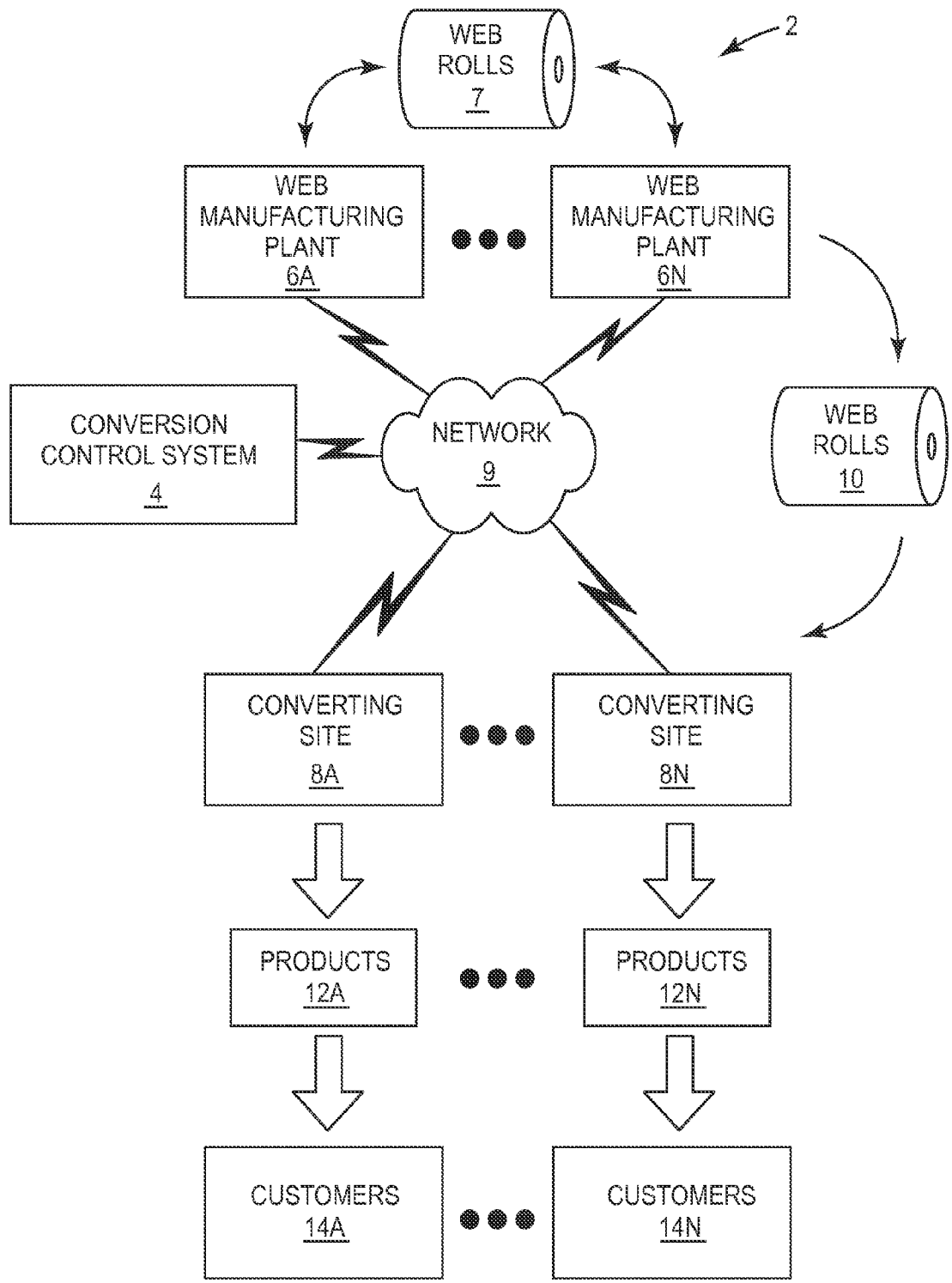
FIG. 1 is a block diagram illustrating a global network environment in which a conversion control system controls conversion of web material.

FIG. 1 is a block diagram illustrating a global network environment 2 in which conversion control system 4 controls conversion of web material. More specifically, web manufacturing plants 6A-6M (web manufacturing plants 6) represent manufacturing sites that produce and ship web material in the form of web rolls 7 between each other and ship finished web rolls 10 to converting sites 8A-8N (converting sites 8). Web manufacturing plants 6 may be geographically distributed, and each of the web manufacturing plants may include one or more manufacturing process lines. Converting sites 8 may be part of the same entity as web manufacturing plants 6. However, in some embodiments, converting sites 8 are consumers of finished web rolls 10. Converting sites 8 may purchase finished web rolls 10 from web manufacturing plants 6 and convert finished web rolls 10 into individual sheets for incorporation into products 12 based on grade levels. That is, the selection process of which sheets should be incorporated into which of products 12 may be based on which of the grade levels each sheet satisfies. In accordance with the techniques described herein, converting sites 8 may also receive data regarding anomalies, i.e. potential defects, in the finished web rolls 10. Ultimately, converting sites 8 may convert finished web rolls 10 into individual sheets which may be incorporated into products 12 for sale to customers 14A-14N (customers 14).

In general, web rolls 7, 10 may contain manufactured web material that may be any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

To produce a finished web roll 10 that is ready for conversion into individual sheets for incorporation into products 12, unfinished web rolls 7 may need to undergo processing from multiple process lines either within one web manufacturing plant, for instance, web manufacturing plant 6A, or within multiple manufacturing plants. For each process, a web roll is typically used as a source roll from which the web is fed into the manufacturing process. After each process, the web is typically collected again into a web roll 7 and moved to a different product line or shipped to a different manufacturing plant, where it is then unrolled, processed, and again collected into a roll. This process is repeated until ultimately a finished web roll 10 is produced.

For many applications, the web materials for each of web rolls 7 may have numerous coatings applied at one or more production lines of one or more web manufacturing plants 6. The coating is generally applied to an exposed surface of either a base web material, in the case of the first manufacturing process, or a previously applied coating in the case of a subsequent manufacturing process. Examples of coatings include adhesives, hardcoats, low adhesion backside coatings, metalized coatings, neutral density coatings, electrically conductive or nonconductive coatings, or combinations thereof. A given coating may be applied to only a portion of the web material or may fully cover the exposed surface of the web material. Further, the web materials may be patterned or unpatterned.

Figure 2:
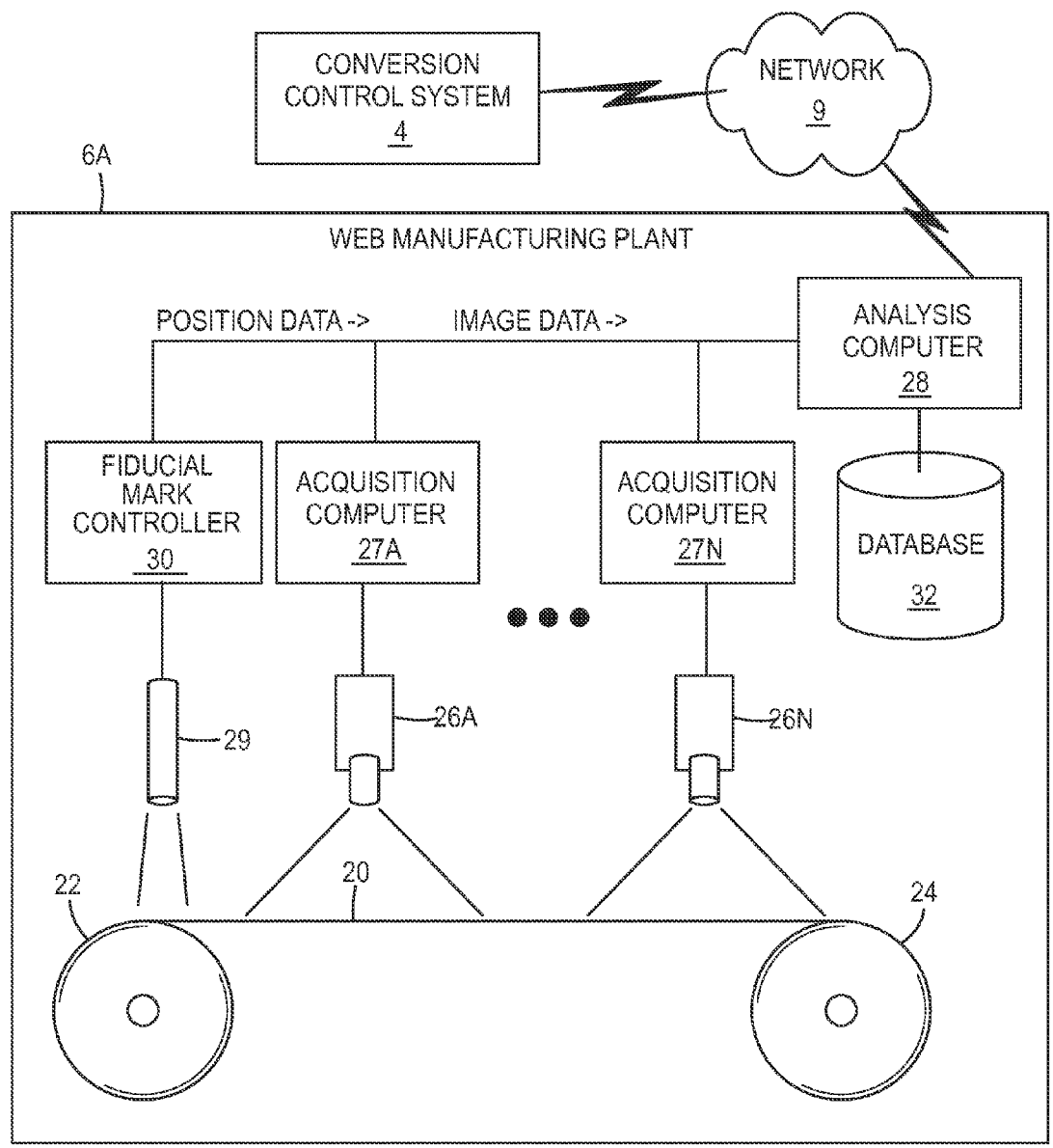
FIG. 2 is a block diagram illustrating an exemplary embodiment of one process line in an exemplary embodiment of a web manufacturing plant.

During each manufacturing process for a given one of web rolls 7, one or more inspection systems acquire anomaly information for the web. For example, as illustrated in FIG. 2, an inspection system for a production line may include one or more image acquisition devices positioned in close proximity to the continuously moving web as the web is processed, e.g., as one or more coatings are applied to the web. The image acquisition devices scan sequential portions of the continuously moving web to obtain digital image data. The inspection systems may analyze the image data with one or more algorithms to produce so called "local" anomaly information. The anomaly information may include a plurality of anomaly objects that represent distinct areas of the web and define a plurality of characteristics for the physical deviations of the web at the corresponding area. An anomaly object may define characteristics such as, for example, a deviation in width of the anomalous area of the web or a deviation in length of an anomalous area of the web. Thus the length and width may represent a physical deviation from predefined characteristics that define, for example, various grade levels. In one exemplary embodiment, image data may be acquired and processed to identify anomalies and to form anomaly objects as data structures representing each anomaly. Information regarding the acquisition and registration of anomaly information is detailed in co-pending patent application "Multi-Unit Process Spatial Synchronization" to Floeder et al., Ser. No. 11/828,369, filed Jul. 26, 2007, assigned to the assignee of the present application, the entire contents of which are hereby incorporated by reference.

In general, conversion control system 4 applies one or more defect detection algorithms that may be application-specific, i.e., specific to products 12, to select and generate a conversion plan for each web roll 10. A certain anomaly may result in a defect in one product, for instance product 12A, whereas the anomaly may not cause a defect in a different product, for instance, product 12B. Each conversion plan represents defined instructions for processing a corresponding finished web roll 10. In accordance with the techniques described herein, conversion control system 4 may communicate the anomaly data for web rolls 10 to the appropriate converting sites 8 for use in converting the web rolls into individual sheets for products 12, e.g. via network 9. In other embodiments, anomaly data may be transferred using computer-readable media such as floppy disks, CD-ROMs, flash memory, or other computer-readable media known in the art.

Figure 4B:
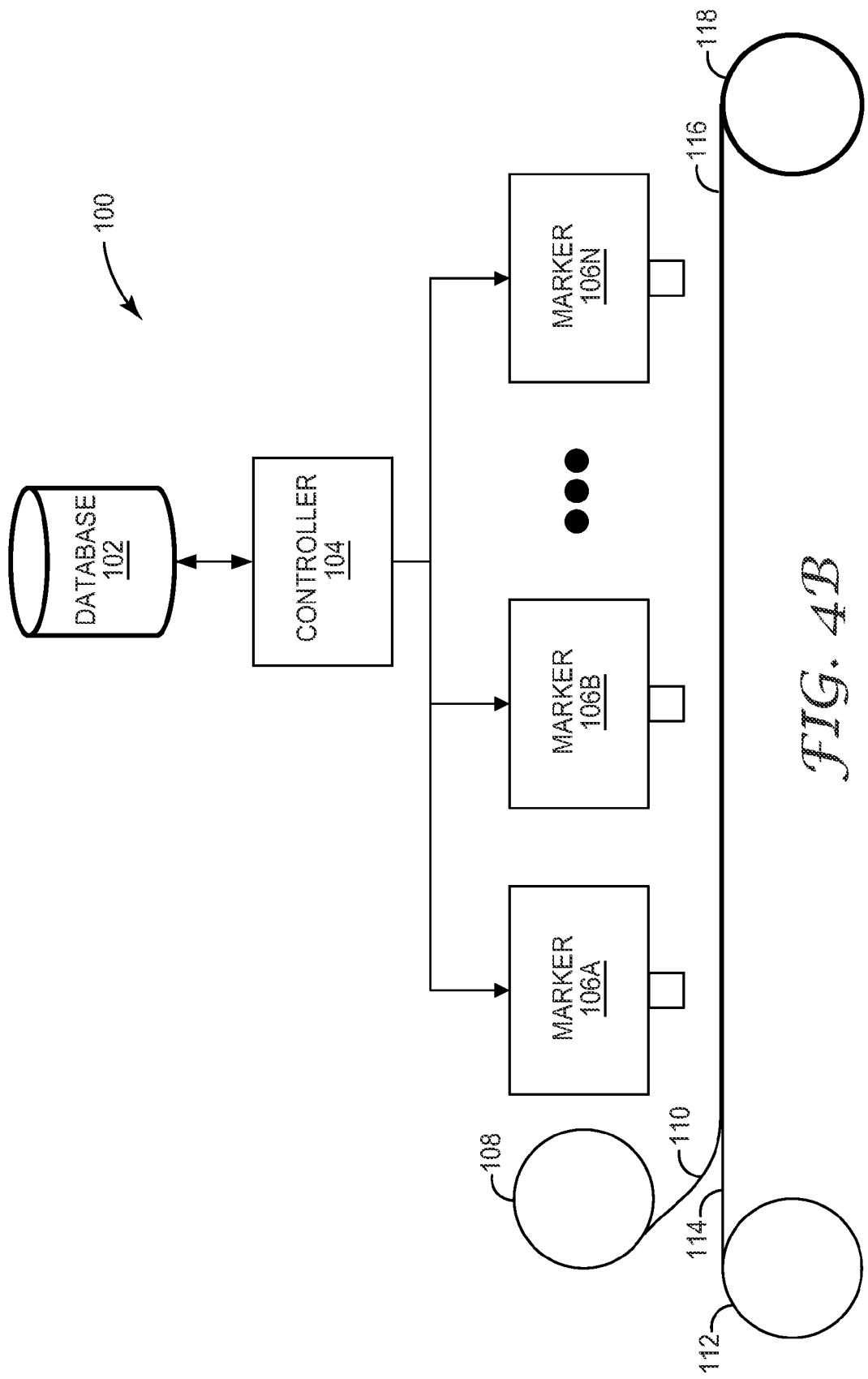
Figure 4C:
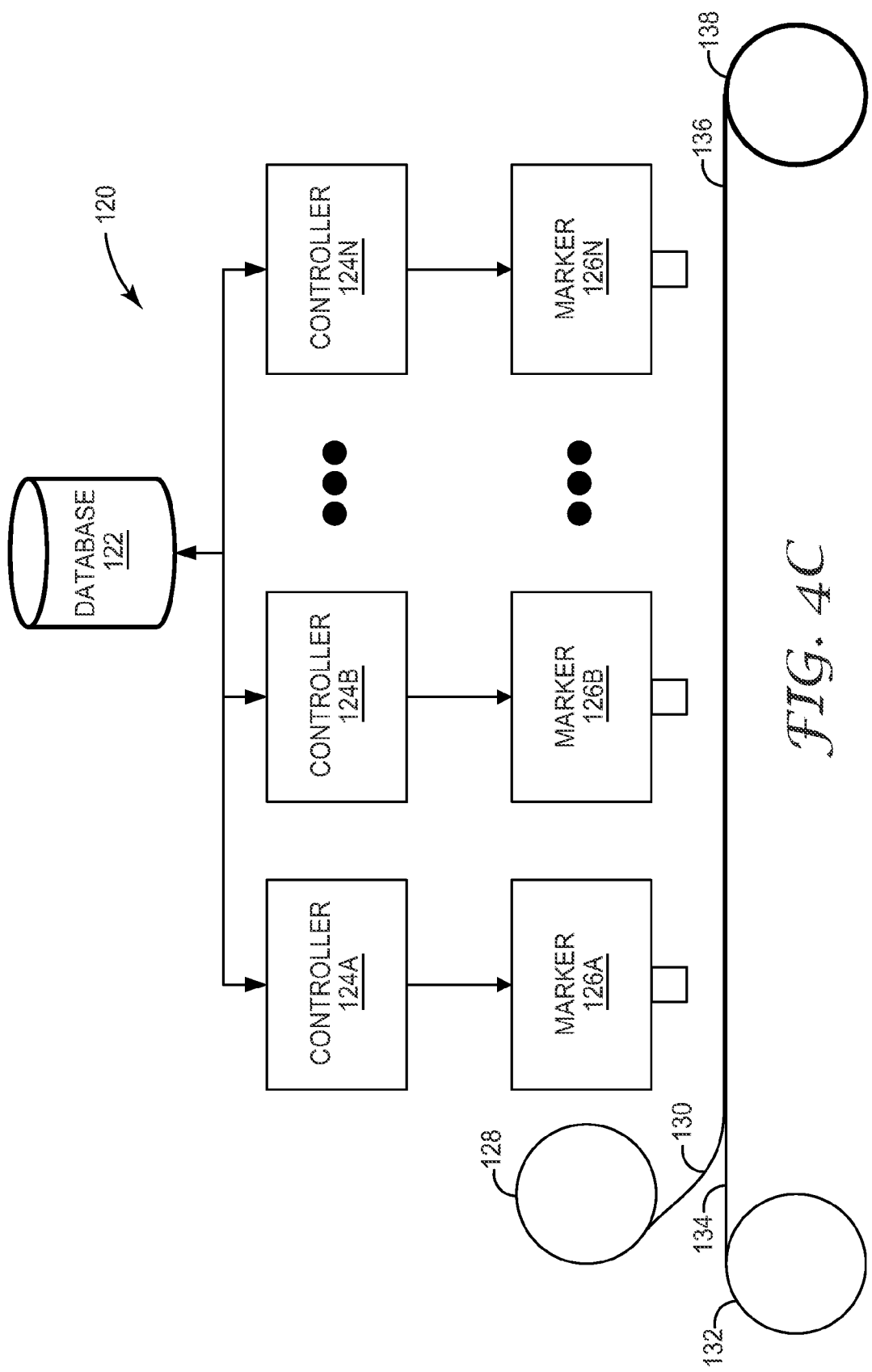

Additionally, one or more of web manufacturing plants 6 may be equipped with an anomaly marking system, as discussed with respect to FIGS. 4A-4C. In general, an anomaly marking system may retrieve the data gathered by the inspection system and mark the positions of anomalies on the surface of the web, or may apply a cover sheet to the web and mark the positions of the anomalies on the cover sheet at the position of the anomaly on the web. A finished web roll 10 may be converted into sheets intended for use in many different products 12. Certain anomalies may cause defects when used only with a subset of products 12. The anomaly marking system may mark the anomalies as well as the products 12 for which the anomaly may cause a defect. Accordingly, converting sites 8 may use the markings to determine which products may still be manufactured from a web region that contains an anomaly.

The techniques described herein may provide several advantages. For example, converting sites 8 of various individual sheets for products 12 from a single finished web roll 10 may determine which regions of the web roll may be most suited for use with each of products 12, for example, according to grade levels of the individual sheets. As another example, producers such as web manufacturing plants 6 may use the anomaly data when determining prices for web rolls 10 for sale to converting sites 8. That is, a finished web roll 10 with fewer anomalies may carry a higher price than a finished web roll 10 with relatively more anomalies. In addition to finished web roll 10, the producer may distribute the anomaly data and markings to a converter so that the converter does not need to re-inspect the web roll for anomalous regions. The producer may save costs from having to separate and discard anomalous regions, while the converter may be able to purchase the web roll and data set at a discount over an anomaly-free web roll or set of web sections. Moreover, the converter may be able to utilize regions with certain anomalies, which might otherwise be discarded, for a product in which the anomaly will not cause a defect, thus salvaging what might otherwise be wasted material.

FIG. 2 is a block diagram illustrating an exemplary embodiment of one process line in an exemplary embodiment of web manufacturing plant 6A of FIG. 1. In the exemplary embodiment, a segment of a web 20 is positioned between two support rolls 22, 24. Image acquisition devices 26A-26N (image acquisition devices 26) are positioned in close proximity to the continuously moving web 20. Image acquisition devices 26 scan sequential portions of the continuously moving web 20 to obtain image data. Acquisition computers 27 collect image data from image acquisition devices 26, and transmit the image data to analysis computer 28 for preliminary analysis.

Image acquisition devices 26 may be conventional imaging devices that are capable of reading a sequential portion of the moving web 20 and providing output in the form of a digital data stream. As shown in FIG. 2, imaging devices 26 may be cameras that directly provide a digital data stream or an analog camera with an additional analog to digital converter. Other sensors, such as, for example, laser scanners, may be utilized as the imaging acquisition device. A sequential portion of the web indicates that the data is acquired by a succession of single lines. Single lines comprise an area of the continuously moving web that maps to a single row of sensor elements or pixels. Examples of devices suitable for acquiring the image include linescan cameras such as those available under the trade designations Model#LD21 from Perkin Elmer (Sunnyvale, Calif.), Piranha Models from Dalsa (Waterloo, Ontario, Canada), or Model Aviiva SC2 CL from Atmel (San Jose, Calif.). Additional examples include laser scanners from Surface Inspection Systems GmbH (Munich, Germany) in conjunction with an analog to digital converter.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

In some embodiments, fiducial mark controller 30 controls fiducial mark reader 29 to collect roll and position information from web 20. For example, fiducial mark controller 30 may include one or more photo-optic sensors for reading bar codes or other indicia from web 20. In addition, fiducial mark controller 30 may receive position signals from one or more high-precision encoders engaged with web 20 and/or rollers 22, 24. Based on the position signals, fiducial mark controller 30 determines position information for each detected fiducial mark. For example, fiducial mark controller 30 may produce position information locating each detected fiducial mark within a coordinate system applied to the process line. Alternatively, analysis computer 28 may place each of the detected fiducial marks within the coordinate system based on the position data received from fiducial mark controller 30. In this case, the position data provided by fiducial mark controller 30 may represent distances between each fiducial mark in a dimension along the length of web 20. In either case, fiducial mark controller 30 communicates the roll and position information to analysis computer 28. Although discussed with respect to fiducial marks and a fiducial mark controller 30 and reader 29, fiducial marks may not be necessary in all embodiments to effect the techniques described herein.

Analysis computer 28 processes image streams from acquisition computers 27. Analysis computer 28 processes the digital information with one or more initial algorithms to generate local anomaly information that identifies any regions of web 20 containing anomalies that may ultimately qualify as defects. Analysis computer 28 may use one algorithm for each of the products 12 into which individual sheets may be incorporated. That is, analysis computer 28 may include a different application-specific defect detection algorithm for each of products 12. Analysis computer 28 may also include a different algorithm for each grade level. Analysis computer 28 may use each algorithm to determine whether an anomaly object represents a defect for each grade level. For each identified anomaly, analysis computer 28 extracts from the image data an anomaly image that contains pixel data encompassing the anomaly and possibly a surrounding portion of web 20. Analysis computer 28 may classify an anomaly into different defect classes if necessary. For instance, there may be unique defect classes to distinguish between spots, scratches, and oil drips. Other classes may distinguish between further types of defects. In accordance with the techniques described herein, analysis computer 28 may further determine in which of products 12 an anomaly may cause a defect. An example technique for analyzing image data to determine the presence and severity of anomalies is discussed in U.S. Pat. No. 7,027,934, titled "Apparatus and Method for Automated Web Inspection," issued to Skeps et al., assigned to the assignee of the present invention, the entire contents of which are hereby incorporated by reference.

In an exemplary embodiment, analysis computer 28 may determine that an anomaly is a defect when the intensity of the anomaly and the size of the anomaly exceed certain thresholds. A first algorithm for a first grade level may determine that an anomaly is a defect when the intensity exceeds a measured value of 50 and the size of the anomaly (determined in pixels) is greater than 10 pixels. A second algorithm for a second grade level may determine that an anomaly is a defect when the intensity exceeds a measured value of 190 and the size of the anomaly is greater than 2 pixels. A third algorithm for a third grade level may determine that an anomaly is a defect when the intensity exceeds a measured value of 30 and the size of the anomaly exceeds 15 pixels. Thus, for a first example anomaly that has an intensity of 200 and a pixel size of 12, an analysis computer 28 running the exemplary algorithms would determine that the first anomaly is a defect for both the first grade level and a second grade level, but not for the third grade level. As described in greater detail below, the analysis computer 28 may instruct one or more markers to mark this first anomaly with both the mark associated with the first grade level and the mark associated with the second grade level. Examples of algorithms are given in Table 1, below, and examples of defects detected by the algorithms are given in Table 2, below:

TABLE 1

| Algorithm | Intensity | Size (pixels) |
|---|---|---|
| A | 50 | 10 |
| B | 190 | 2 |
| C | 30 | 15 |

TABLE 2

| Anomaly | Intensity | Size (pixels) | Defect In: |
|---|---|---|---|
| 17862 | 200 | 12 | A, B |
| 17863 | 100 | 5 | None |
| 17864 | 45 | 17 | C |
| 17865 | 70 | 11 | A |
| 17866 | 195 | 4 | B |
| 17867 | 198 | 16 | A, B, C |

Based on the position data produced by fiducial mark controller 30, analysis computer 28 determines the spatial position of each anomaly within the coordinate system of the process line. That is, based on the position data from fiducial mark controller 30, analysis computer 28 determines the x, y, and possibly z position for each anomaly within the coordinate system used by the current process line. For example, a coordinate system may be defined such that the x dimension represents a distance across web 20, a y dimension represents a distance along a length of the web, an the z dimension represents a height of the web, which may be based on the number of coatings, materials or other layers previously applied to the web. Moreover, an origin for the x, y, z coordinate system may be defined at a physical location within the process line, and is typically associated with an initial feed placement of the web 20.

In any case, analysis computer 28 records in database 32 the spatial location of each anomaly with respect to the coordinate system of the process line, this information being referred to herein as local anomaly information. That is, analysis computer 28 stores the local anomaly information for web 20, including roll information for the web 20 and position information for each anomaly, within database 32. Analysis computer 28 may also record, for each anomaly, those products 12 for which the anomaly may cause a defect. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, database 32 is implemented as a relational database provided by SQL Server™ from Microsoft Corporation.

Once the process has ended, analysis computer 28 will transmit the data collected in database 32 to conversion control system 4 via network 9. Specifically, analysis computer 28 communicates the roll information as well as the local anomaly information and respective sub-images to conversion control system 4 for subsequent, offline, detailed analysis. For example, the information may be communicated by way of a database synchronization between database 32 and conversion control system 4. In some embodiments, conversion control system 4 may determine those products of products 12 for which each anomaly may cause a defect, rather than analysis computer 28. Once data for the finished web roll 10 has been collected in database 32, the data may be used to mark anomalies on the web roll, either directly on the surface of the web with a removable or washable mark, or on a cover sheet that may be applied to the web before or during marking of anomalies on the web.

FIGS. 3A-3D (FIG. 3) are block diagrams illustrating exemplary systems for inspecting a web and marking anomalies on the web. Many different systems may perform the techniques described herein. That is, the tasks of production of a web, inspection of a web, and preferentially marking anomalies and/or defects on a web may be part of a single line, two of the tasks may be on one line while the other is part of a different line, or each may be on a separate line. Moreover, various elements of each task may be performed by either the web producer or a web converter who may purchase the finished web roll, e.g. web roll 10, from the producer for conversion into individual sheets for incorporation into products 12.

Figure 3A:
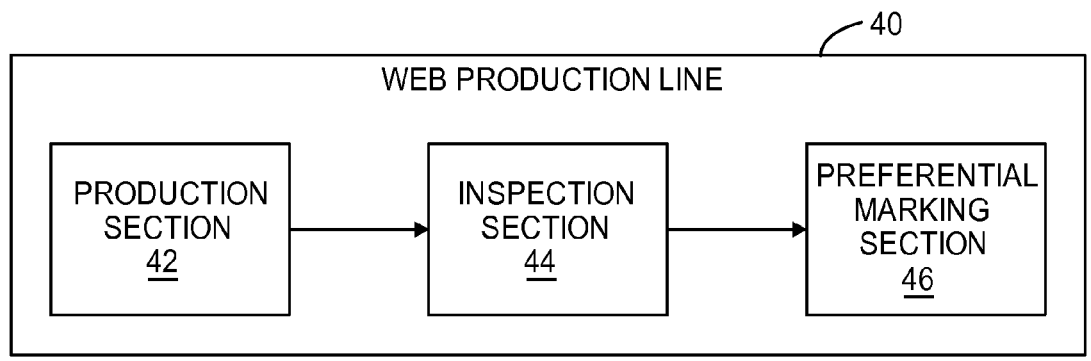
FIGS. 3A-3D are block diagrams illustrating exemplary systems for inspecting a web and marking anomalies on the web.

The exemplary embodiment of FIG. 3A depicts a single web production line 40 that includes a production section 42, an inspection section 44, and a preferential marking section 46. Production section 42 of web production line 40 performs manufacturing operations on a finished web roll 10. Inspection section 44 may perform tasks similar to those described with respect to FIG. 2, i.e. digital imaging of a web and data storage into a database, e.g. database 32 of FIG. 2. A web roll may begin at production section 42 for manufacturing, traverse inspection section 44 for inspection, and be marked at preferential marking section 46 before being collected onto a roll at the end in one exemplary embodiment.

Preferential marking section 46 may retrieve data stored in the database to mark the positions of anomalies on the surface of, or on a cover sheet of, web roll 10. Preferential marking section 46 may obtain data regarding what may be regarded as a defect in each potential product for web roll 10. Preferential marking section 46 may also acquire data regarding the potential products 12 into which individual sheets from web roll 10 may be incorporated. Preferential marking section 46 may be equipped with markers (not shown) for each of products 12, i.e. one unique marker for each of products 12. Preferential marking section 46 may then use the data collected at inspection section 44 such that, for each anomaly, preferential marking section 46 may place a mark on the anomaly for each of the products 12 for which the anomaly may cause a defect.

As an example, a finished web roll 10 may form the base from which individual sheets are cut for three different products 12: product A, product B, and product C. Preferential marking section 46 may associate a unique mark with each of products A, B, and C. For example, the mark for product A may be a square, the mark for product B may be a circle, and the mark for product C may be a triangle. If an anomaly may cause a defect in products A and C, but not in B, preferential marking section 46 may apply a square mark and a triangle mark to the anomaly. Greater details with respect to the application of marks to a web are discussed with respect to FIGS. 5A-5C. Techniques for applying and using fiducial marks to identify specific locations on a web are described in co-pending patent application "Apparatus and Method for the Automated Marking on Webs of Material" to Floeder et al., assigned to the assignee of the present application, Ser. No. 10/826,995, filed Apr. 19, 2004, the entire contents of which are hereby incorporated by reference.

Figure 3B:
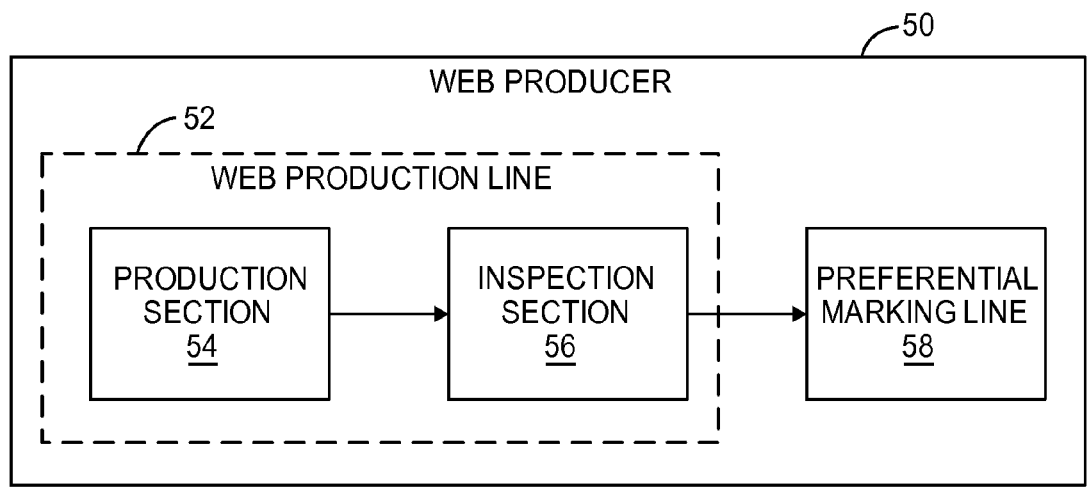

FIG. 3B is another exemplary embodiment wherein a web producer 50 performs the acts of producing, inspecting, and preferentially marking a web. However, in this example embodiment, web production line 52 has production section 54 and inspection section 56, while preferential marking line 56 performs the preferential marking of web roll 10. That is, in this exemplary embodiment, a web roll 10 undergoes production and inspection on web production line 52 at production section 54 and inspection section 56, respectively. However, web roll 10 must be collected onto a roll and then transferred to a different line, i.e. preferential marking line 56, where marks are applied to the positions of the anomalies.

In some embodiments, in order for two different production lines to locate positions of anomalies on a web, the web may be equipped with fiducial marks. Likewise, the production lines may be equipped with fiducial mark readers as discussed with respect to FIG. 2. Techniques for using fiducial marks with a web are discussed in co-pending patent application "Fiducial Marking for Multi-Unit Process Spatial Synchronization," Ser. No. 11/828,376, to Floeder et al., assigned to the assignee of the present application, filed Jul. 26, 2007, the entire contents of which are hereby incorporated by reference. In the manner described therein, two production lines may accurately locate the same point on a web using fiducial marks placed along the edge of the web. Moreover, according to the techniques described therein, it may be possible to locate such a position even if the web stretches, shrinks, is combined with another web, loses a section of existing web, or in any way changes size. Other embodiments may use other locating methods without departing from the techniques described herein.

Figure 3C:
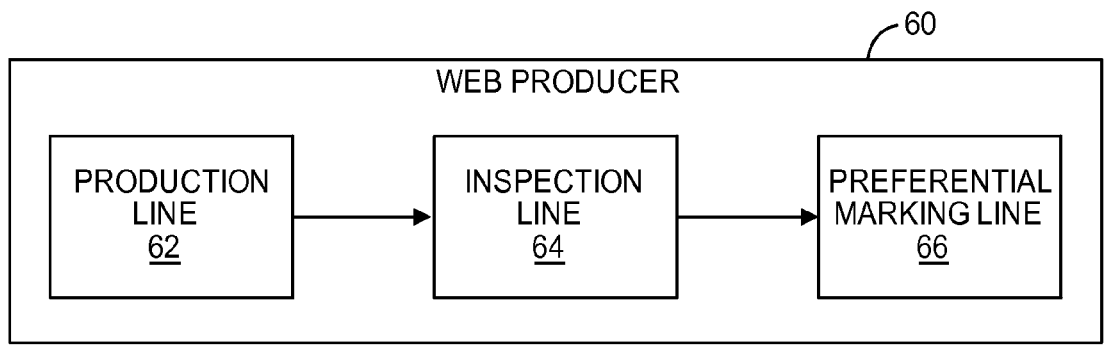

FIG. 3C is yet another exemplary embodiment wherein the web producer 60 performs the acts of producing, inspecting, and preferentially marking a web. In this embodiment, each of these tasks is performed at a distinct line, i.e. production line 62, inspection line 64, and preferential marking line 66, respectively. Thus the techniques described herein are not limited to production, inspection, and marking each occurring on the same line. It is also possible for the production line to be a single line and for another line to include both an inspection area and a preferential marking area, although this embodiment is not shown in the figures.

Figure 3D:
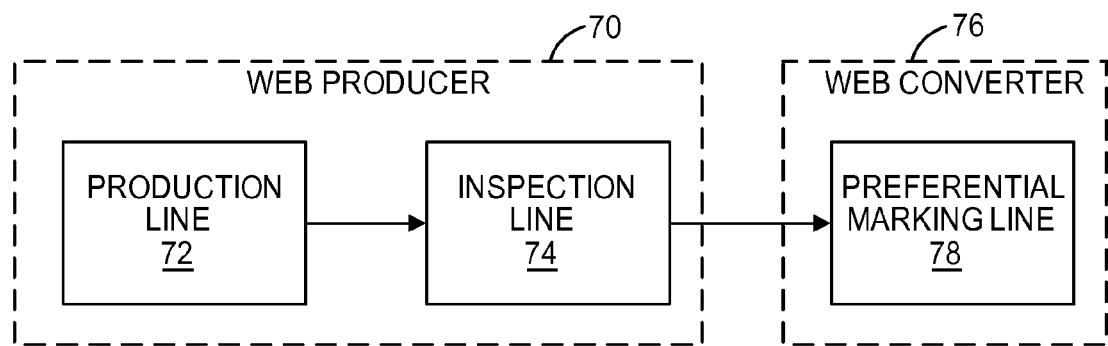

FIG. 3D is another exemplary embodiment wherein the web producer 70 produces and inspects a finished web roll 10, which may be ready for division into individual sheets for incorporation into products 12, using production line 72 and inspection line 74, respectively. However, web producer 70 may transfer finished web roll 10 to web converter 76 without actually marking the locations of the anomalies on web roll 10. Web converter 76 may be a distinct entity that purchases finished web rolls 10 and then converts web rolls 10 into individual sheets for products 12. Additionally, web producer 70 may transfer the data acquired by inspection line 74 to web converter 76. Web converter 76 may be able to acquire a web roll 10 at a discounted rate from web producer 70, based upon the number of anomalies present in web roll 10, while web converter 76 may save on costs because web converter 76 need not inspect web roll 10 to discover anomalies. Web producer 70 may also save on costs because web producer 70 need not isolate and remove anomalous regions of web roll 10.

FIGS. 4A-4C (FIG. 4) are block diagrams illustrating exemplary embodiments of web marking systems according to the techniques described herein. Any of the web marking systems of FIG. 4 may perform the tasks of any of the exemplary embodiments of preferential marking lines or sections of FIG. 3. For example, web marking system 80 of FIG. 4A may perform the functions of preferential marking section 46 of FIG. 3A.

FIG. 4A depicts one exemplary embodiment of a web marking system 80. Database 82 may correspond to database 32 of FIG. 2, or database 82 may receive or retrieve data from another database, e.g. database 32. For example, controller 84 may be connected to database 82 via a network (not shown) when database 82 corresponds to database 32 of FIG. 2. As another example, database 82 may receive a copy of the data stored on database 32, e.g. over a network or on flash memory, and controller 84 may retrieve the data from local database 82. In any case, database 82 of FIG. 4A stores data regarding anomalies on a finished web roll 10. This data may be collected by an inspection system, for example, the inspection system depicted in and described with respect to FIG. 2.

A web roll, e.g. web roll 10, may be loaded onto web spool 92. Additionally, covering material 90 may be applied to the web with a covering applicator 88 to protect web surface 94 and to receive anomaly markings. For example, a roll of cover sheet 90 may be loaded onto cover sheet spool 88. Cover sheet 90 may be placed over the surface of web 94 to form covered web 96, which may be collected onto collecting spool 98. That is, collecting spool 98 may collect web 94 with cover sheet 90 covering web 94. Cover sheet 90 may be a sheet that is receptive to marks made by marker 86. For example, cover sheet 90 may be made of paper, woven cloth, plastic laminate, clear plastic sheeting, or other types of material. Cover sheet 90 may be receptive to colored inks, burning (e.g. by a laser printer), scratches, dents, or any other suitable markings. In some embodiments, a covering material may be formed from a material that can be poured onto web surface 94 and hardened to a degree that enables mark application and reception but that does not prevent covered web 96 from being collected onto collecting spool 98. In yet another embodiment, the web may be cut into sections rather than being collected onto collecting spool 98. In another embodiment, marker 86 may apply marks directly to web surface 94 without a cover sheet. In such a case, the mark may be removable or washable without damaging web surface 94 and without being removed when collected onto collecting spool 98.

Controller 84 retrieves data from database 82 regarding positions of anomalies on web surface 94. Controller 84 distinguishes between anomalies for each of products 12. That is, controller 84 analyzes each anomaly to determine each of products 12 for which the anomaly may cause a defect. For each anomaly, controller 84 instructs marker 86 to place marks corresponding to each of products 12 in which the anomaly may cause a defect.

Figure 5A:
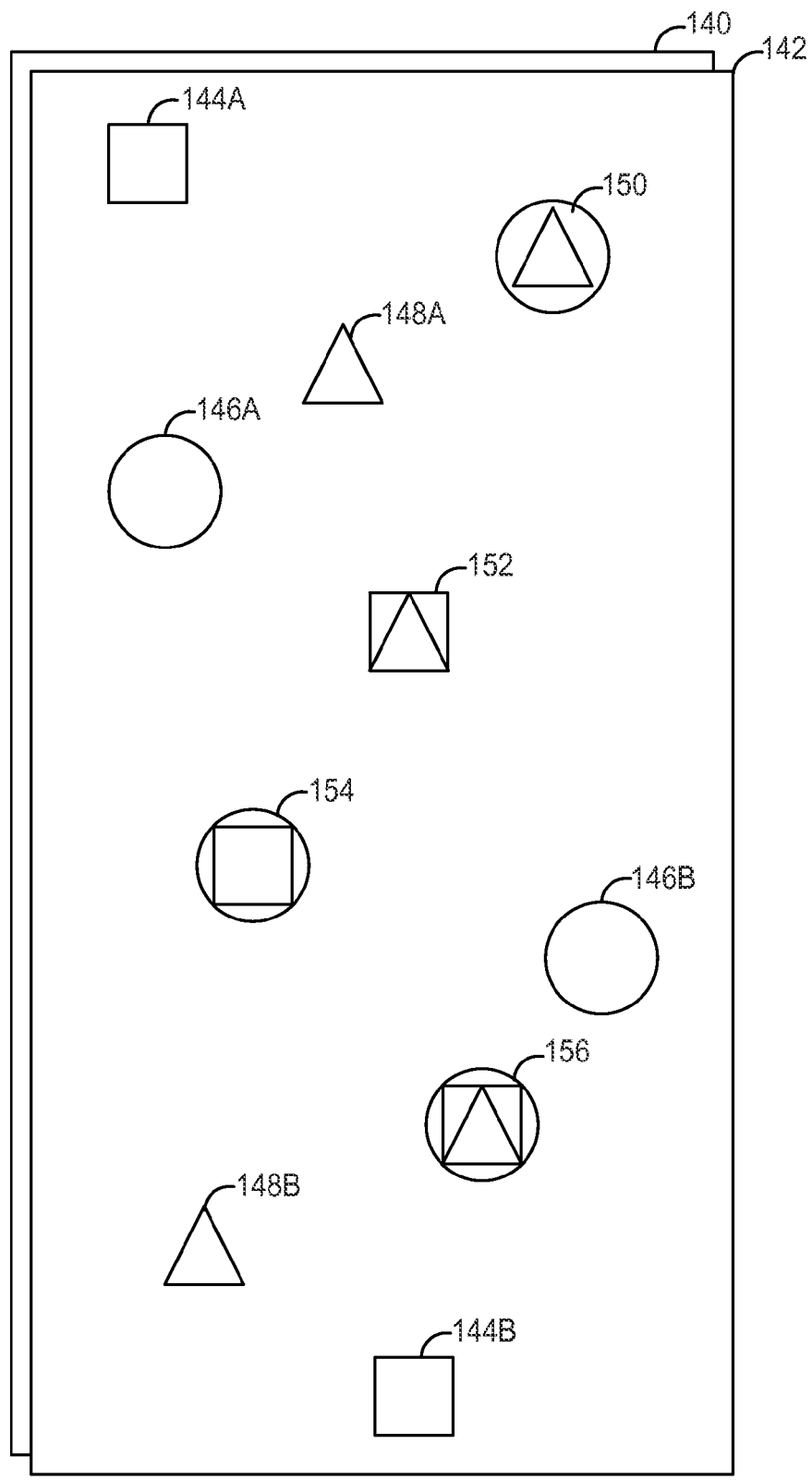
FIGS. 5A-5C are block diagrams illustrating exemplary marks that may identify positions of anomalies on a web.
Figure 5B:
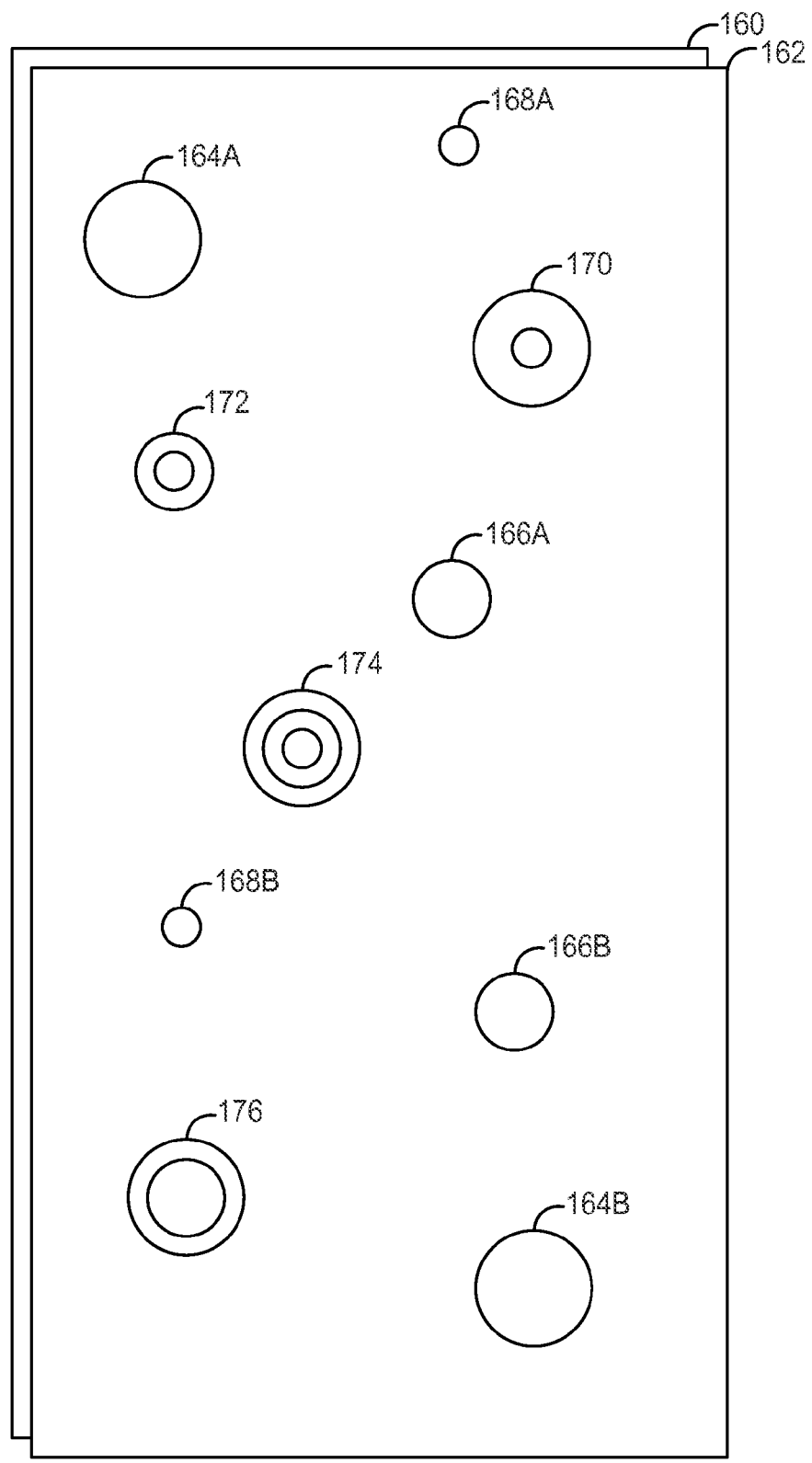
Figure 5C:
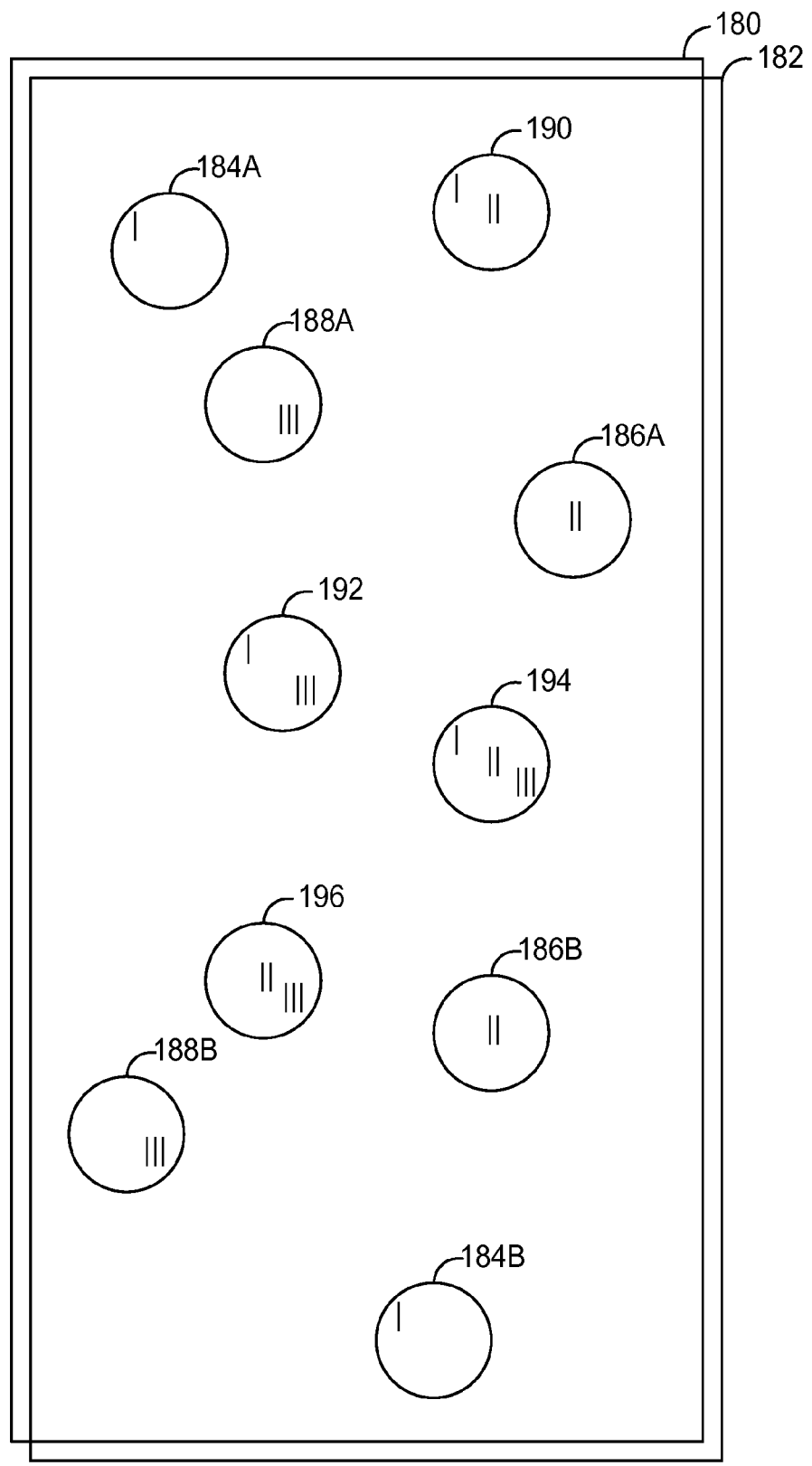

Marker 86 is capable of printing a plurality of marks simultaneously. Marker 86 may be, for example, a laser printer, a laser jet printer, an ink jet printer, a multi-color printer, or any other device capable of making a mark on web surface 94 or cover sheet 96. Marker 86 may also be capable of traversing the web in the cross-web direction, i.e. orthogonally to the direction of the movement of the web. Therefore, marker 86 may be able to place a mark at or substantially near the precise position of the anomaly in both the cross-web and down-web axes. Examples of these markings are depicted in FIGS. 5A-5C.

FIG. 4B depicts another example embodiment of a web marking system 110 similar to that shown in FIG. 4A. Database 102 may correspond to database 82, controller 104 may be similar to controller 84, cover sheet spool 108 may correspond to cover sheet spool 88, cover sheet 110 may correspond to cover sheet 90, web spool 112 may correspond to web spool 92, web surface 114 may correspond to web surface 94, covered web 116 may correspond to covered web 96, and collecting spool 118 may correspond to collecting spool 98.

However, rather than having a single marker as in the example of FIG. 4A, web marking system 100 includes a plurality of web markers 106A-106N (web markers 106). Each of web markers 106 may be dedicated to making a specific mark. For example, web marker 106A may only mark a square on web surface 114 or cover sheet 110, whereas web marker 106B may only mark a circle on web surface 114 or cover sheet 110. Each of web markers 106 may also be loaded with a different color of ink when web markers 106 use ink to make a mark. Like web marker 86, web markers 106 may be enabled to traverse the web in the cross-web direction to apply the mark at the position of the anomaly.

In one embodiment, one of web markers 106, such as web marker 106A, may place a mark on or around an anomaly, while other web markers, such as web markers 106B-106N, may correspond to products 12 into which individual sheets from web roll 10 may be incorporated to indicate whether the marked anomaly may cause a defect in that product. For example, web marker 106A may place a circle around an anomaly, while web markers 106B-106N may place a number of hash marks at a certain location to indicate whether the anomaly may cause a defect in the associated one of products 12. One example of this embodiment is discussed with respect to FIG. 5C.

Controller 104 controls each of web markers 106. Controller 104 again retrieves data from database 102 and determines for each anomaly whether the anomaly may cause a defect for each of products 12. Controller 104 determines each of the products 12 for which an anomaly may cause a defect and signals the corresponding ones of web markers 106 to place a mark at the anomaly. For example, if an anomaly may cause a defect in product A and product B, and web marker 106A makes a mark associated with product A and web marker 106B makes a mark associated with product B, controller 104 may signal web markers 106A and 106B to place a mark at the position of the anomaly on web surface 114 or cover sheet 110. Each of web markers 106 may be placed a certain distance apart in the down-web direction. In one embodiment, this spacing may be five inches. In any case, controller 104 may be programmed with the positions of each of web markers 106, as well as the distance between each neighboring web marker.

FIG. 4C depicts yet another example embodiment of a web marking system 120, similar to that shown in FIG. 4A. Database 122 may correspond to database 82, cover sheet spool 128 may correspond to cover sheet spool 88, cover sheet 130 may correspond to cover sheet 90, web spool 132 may correspond to web spool 92, web surface 134 may correspond to web surface 94, covered web 136 may correspond to covered web 96, and collecting spool 138 may correspond to collecting spool 98.

However, web marking system 120 has a one-to-one relationship between controllers 124A-124N (controllers 124) and web markers 126A-126N (web markers 126). That is, controller 124A is associated only with web marker 126A, controller 124B is associated only with web marker 126B, and so on. Each of controllers 124 retrieves data from database 122. However, controller 124A is associated with a particular product, for example, product A. Therefore, controller 124A retrieves anomaly data from database 122 only for anomalies that may cause a defect in product A. Similarly, controller 124B only retrieves anomaly data for anomalies that may cause a defect in product B, and so on.

Likewise, web markers 126 are similar to web markers 106 of FIG. 4B, in that web markers 126 may be dedicated to applying only a single type of mark to web surface 134 or cover sheet 130. Each of web markers 126 may also be loaded with a different color of ink when ink is used to mark the locations of anomalies. When controller 124A determines that an anomaly may cause a defect in product A, controller 124A signals web marker 126A to apply a mark at the position of the anomaly. Similarly, when controller 124B determines that an anomaly may cause a defect in product B, controller 124B signals web marker 126B to apply a mark at the position of the anomaly, and so on. Each of web markers 126 may be spaced approximately the same distance apart, for example, five inches down-web.

FIGS. 5A-5C (FIG. 5) are block diagrams illustrating exemplary marks that may identify positions of anomalies on a web. In general, there may be one unique mark for each of products 12. Any type of distinguishing mark may be used to identify anomalies and those of products 12 in which each anomaly may cause a defect. Therefore the techniques described herein are not limited to these exemplary marks. Moreover, although the examples of FIG. 5 include three unique markings, the techniques described herein are not limited to any particular number of unique markings. The sizes of the marks depicted in FIG. 5 are not necessarily to scale with the width of the web. In one embodiment, a web may be approximately sixty inches cross-web, and a mark may be a six inch diameter circle. However, the techniques described herein are not limited to any particular sizes of either a web or of markings.

In the example of FIG. 5A, various geometric shapes are used to identify positions of anomalies of web 140. Additionally, the shapes may be of different colors to help further distinguish the marks, if the marks are made in ink. The marks may be applied directly to web surface 140 or onto a cover sheet, i.e. cover sheet 142. In this example, square marks are associated with product A, circle marks are associated with product B, and triangle marks are associated with product C. Square marks 144A and 144B indicate positions of anomalies that may cause defects in product A. Circle marks 146A and 146B indicate positions of anomalies that may cause defects in product B. Triangle marks 148A and 148B indicate anomalies that may cause defects in product C.

Mark 150, comprising both a circle mark and a triangle mark, indicates an anomaly that may cause a defect in both products B and C. Mark 152, comprising a triangle and a square, indicates an anomaly that may cause a defect in both products A and C. Mark 154, comprising a circle and a square, indicates an anomaly that may cause a defect in both products A and B. Mark 156, comprising a square, a circle, and a triangle, indicates an anomaly that may cause a defect in each of products A, B, and C.

A conversion system may be equipped to recognize various geometric shapes, e.g. circles, triangles, and squares. The conversion system may also be equipped to determine the products to assemble from various sheets converted from the web in accordance with the anomaly markings. For example, the system may be programmed to prioritize products A, B, and C, or to select between products A, B, and C in some manner. The conversion system may recognize square mark 144A, for example, and automatically determine whether to use this section of the web for conversion into product B or product C. Likewise, the conversion system may reject the web section marked by mark 156 as not being useful for any of products A, B, or C. The conversion system may further be equipped to automatically remove cover sheet 142 from the web section of web 140 before converting web 140 into sheets for assembly into the selected product.

FIG. 5B depicts another example embodiment wherein various sizes of circles are used to identify positions of anomalies of web 160. The marks may be applied directly to web surface 160 or onto a cover sheet, i.e. cover sheet 162. The marks may be, for example, two inch diameter circles 168A and 168B associated with product A, four inch diameter circles 166A and 166B associated with product B, and six inch diameter circles 164A and 164B associated with product C. Moreover, the circles may be printed in different colors of ink to further aid in distinguishing with which products each mark is associated.

Mark 170, comprising a two inch diameter circle and a six inch diameter circle, indicates the position of an anomaly that may cause a defect in products A and C. Mark 172, comprising a two inch diameter circle and a four inch diameter circle, indicates the position of an anomaly that may cause a defect in products A and B. Mark 174, comprising a two inch diameter circle, a four inch diameter circle, and a six inch diameter circle, indicates the position of an anomaly that may cause a defect in products A, B, and C. Mark 176, comprising a four inch diameter circle and a six inch diameter circle, indicates the position of an anomaly that may cause a defect in products B and C.

FIG. 5C indicates yet another example embodiment wherein a circle is used to indicate the position of an anomaly and various numbers of hash marks in certain positions within the circle are used to indicate association with products A, B, and C. That is, a single hash mark in the upper left of the circle is associated with product A, two hash marks in the center of the circle is associated with product B, and three hash marks in the bottom right of the circle is associated with product C. Again, these marks may be placed directly on the surface of the web 180 or on a cover sheet 182.

Marks 184A and 184B indicate the positions of anomalies that may cause defects in product A. Marks 186A and 186B indicate the positions of anomalies that may cause defects in product B. Marks 188A and 188B indicate the positions of anomalies that may cause defects in product C. Mark 190 indicates the position of an anomaly that may cause a defect in products A and B. Mark 192 indicates the position of an anomaly that may cause a defect in products A and C. Mark 194 indicates the position of an anomaly that may cause a defect in products A, B, and C. Mark 196 indicates the position of an anomaly that may cause a defect in products B and C.

In one embodiment, the preferential marking system may use one marker to mark the circle that indicates the presence of an anomaly and subsequent markers are used to indicate those products for which the anomaly may case a defect. In other embodiments, each marker may make the circle mark as well as the associated hash marks. In still other embodiments, one marker may make the circle and all hash marks therein.

Figure 6:
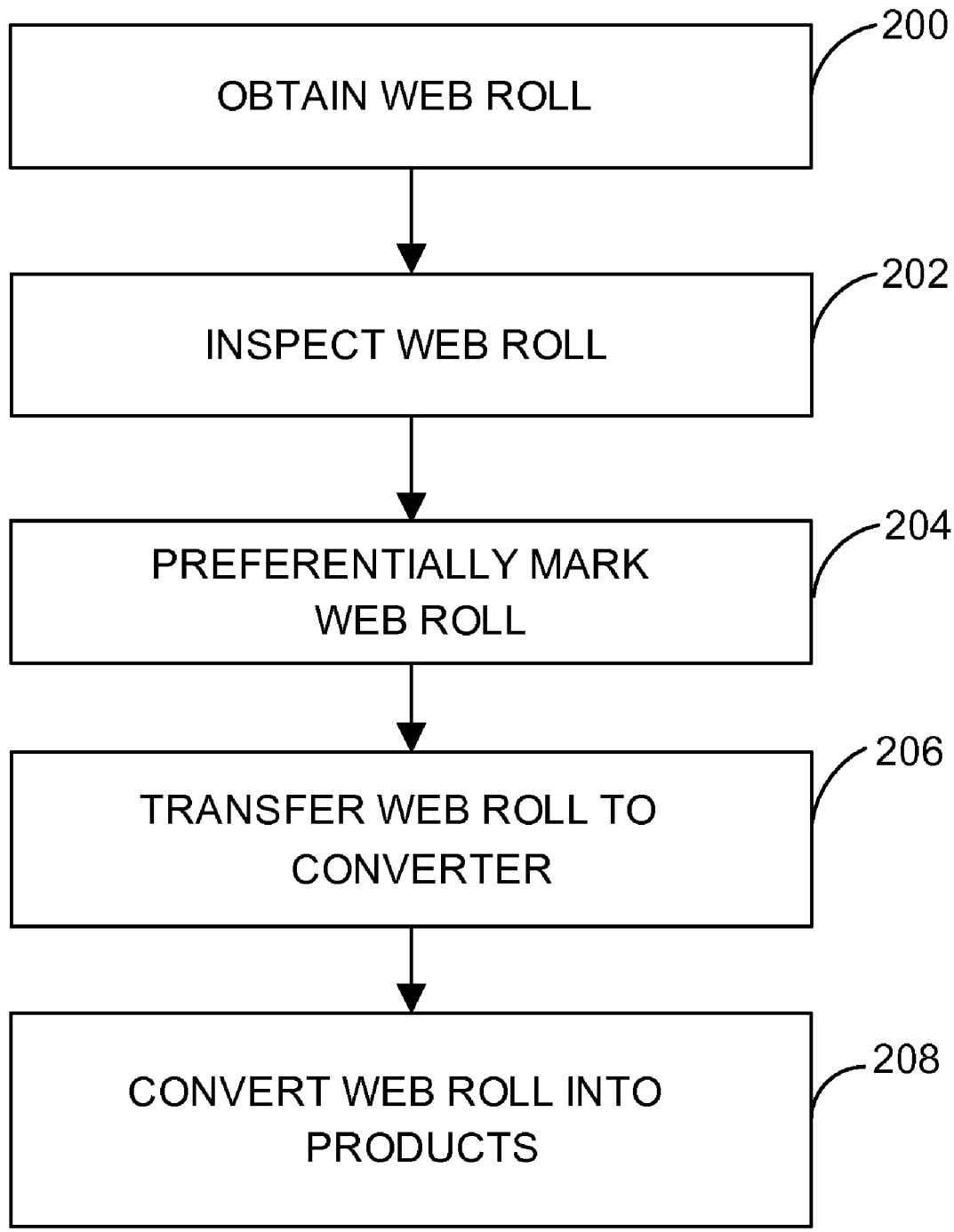
FIG. 6 is a flow chart illustrating an exemplary method of inspecting and marking a web roll according to the techniques described herein.

FIG. 6 is a flow chart illustrating an exemplary method of inspecting and marking a web roll according to the techniques described herein. First, a web roll, such as web roll 10, is obtained (200). Obtaining a web roll may be either through producing the web roll or by purchasing or receiving a web roll from a producer. Next, the web roll is inspected for anomalies (202). An inspection system, such as that discussed with respect to FIG. 2, may be used to inspect the web. The inspection system may inspect web roll 10 according to various products 12 into which individual sheets from the web roll may be incorporated. The inspection system may be designed to particularly search for and record data regarding known anomalies that may cause defects for each of products 12 into which individual sheets from the web roll may be incorporated. The inspection system may record the presence of an anomaly, the location of the anomaly, and each of the potential products 12 for which the anomaly may cause a defect. For example, the inspection system may record this data in a database, such as database 32 of FIG. 2.

Next, the locations of the anomalies may be marked on the web roll 10 (204). Anomalies may be marked directly on the surface of the web roll, or they may be marked on a cover sheet that covers the web roll and that is designed to receive a marking. The web roll producer/inspector may be the one to mark the locations of anomalies on the web roll. The producer may then transfer the marked web roll to the converter (206). The converter may analyze the web roll, cut the web roll into sheets, and assemble the sheets into products (208). The converter may use any selection mechanism for determining which sections should be assembled into which products. For example, the converter may prioritize the products and assemble each section into the highest priority product. As another example, the converter may attempt to analyze the probability of an anomaly causing a defect in each product and choose the product corresponding to the lowest probability for assembly.

In an alternative embodiment, the producer/inspector may transfer the web roll to a converter, along with the anomaly data, without marking the positions of anomalies on the web. Then the converter may use the anomaly data to mark the positions of anomalies on the web. As yet another alternative, the converter may use the data to directly sort the web into sections, each of which may be destined for a different product for conversion. That is, rather than performing the extra step of marking the locations of anomalies on the web, the converter may simply determine the products into which a particular section of the web can be converted. If there are products that the section may not be used for while others that the section can be used for, the converter can select the product that the section may best be used for and directly assemble the section into that product (208) without ever actually marking the position of the anomaly on the web.

Figure 7:
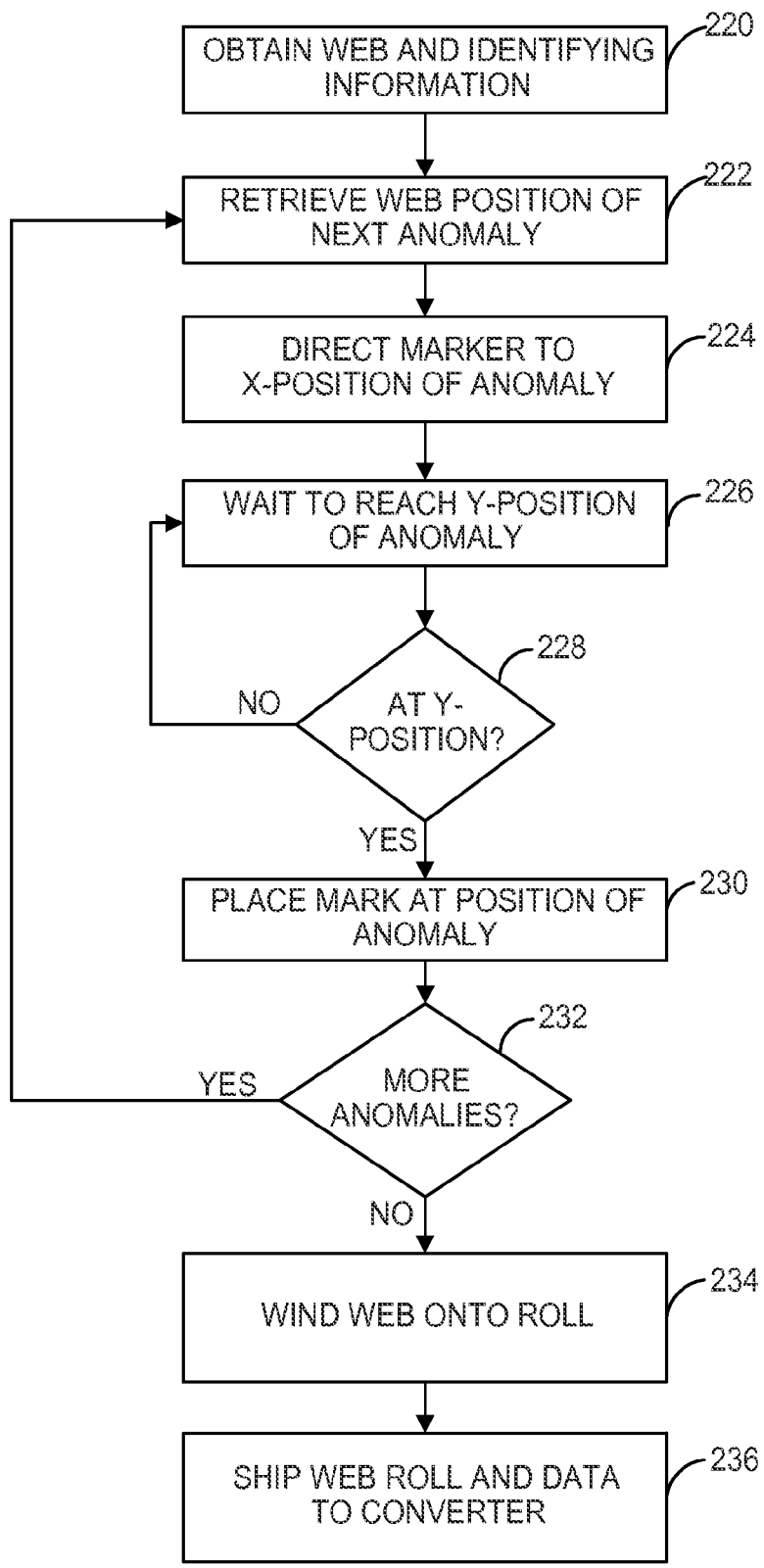
FIG. 7 is a flow chart illustrating an exemplary method of marking positions of anomalies of a web roll.

FIG. 7 is a flow chart illustrating an exemplary method of marking positions of anomalies of a web roll. For the purposes of this flowchart, anomalies are identified by an x-position and a y-position, such that the y-position is a position on an axis parallel to the direction of the movement of the web (i.e., the y-position determines down-web position), and the x-position is a position on an axis orthogonal to the y-position (i.e., the x-position determines the cross-web position).

First, a finished web roll 10 and its corresponding identifying information are obtained (220). The identifying information is used to locate anomaly information about the web roll 10 in a database, e.g. database 32 of FIG. 2. In one embodiment, a web producer may obtain a web roll 10 by first manufacturing the web roll. In another embodiment, a web producer may obtain a web roll 10 by manufacturing the web roll at another manufacturing plant and transferring the finished web roll 10 to an inspection/marking line. In yet another embodiment, a web converter may obtain a web and corresponding data from a web producer after the web producer has produced and inspected a finished web roll 10.

Next, the identifying information is used to retrieve the position of the first anomaly on the web from the database (222). Included in this data retrieval may be the cross-web position of the anomaly as well as the identity of those products for which the anomaly may cause a defect. In some embodiments, such as that portrayed in FIGS. 4A and 4B, a single marker controller may retrieve all of this data. In other embodiments, such as the example of FIG. 4C, there may be one marker controller associated with each product, thus the controller may retrieve data regarding the first anomaly that may cause a defect in the product associated with the controller. That is, the controller may ignore anomalies that will not cause defects in the product with which the controller is associated. In this embodiment, each controller, as well as the associated marker, may act independently of each other controller/marker combination.

In any case, once the controller has retrieved the position of the anomaly, the controller may direct the marker to the x-position, i.e. the cross-web position, of the anomaly (224). In some embodiments, the marker may be movably mounted on bars or cables over the moving web. In other embodiments, the marker may direct a laser beam using one or more mirrors. Other suitable means may also be used for making a mark on the web or cover sheet. In any case, the marker may be positioned at the x-position of the anomaly such that the marker is ready to mark when the y-position arrives. The controller may then wait until the proper y-position on the web is reached (226). If the y-position is not yet reached, the controller may continue to wait (228). If the controller is associated with multiple markers, the controller may determine the y-positions of each marker relative to the other markers in order to properly determine when the y-position has been reached for each marker that must make a mark over the anomaly. If there is one controller for each marker, each controller may determine whether the y-position has been reached for its associated marker.

Once the y-position of the anomaly has been reached, the controller may signal the marker to make a mark at the position of the anomaly (230). If the marker is equipped to make a plurality of different marks, the controller may signal the marker as to which marks the marker should make. If the marker is dedicated to making a single type of mark, the controller may signal the marker to make the mark. The marker, in response to this signal, may make the mark on the web or on the cover sheet over the web.

If there are more anomalies (232), the steps of 222-230 will repeat until there are no more anomalies, i.e. until all known anomalies have been marked according to the collected data. Otherwise, the web will be completely collected onto the gathering roller (234). The web may then be shipped to the converter for conversion into sheets for assembly into products according to the markings on the web (236).

In some embodiments, the data from which anomalies were determined may also be transferred to the converter. The converter may use this data to make more detailed analysis regarding the conversion of the web into individual sheets for assembly into products 12. The converter may also attempt to use sections of the web that have been marked as anomalous for each of products 12 for conversion into sheets that may be assembled into a new or different product for which the web roll may not have originally been intended in order to reduce waste material. In some embodiments, the web may be delivered in roll form to the converter. In some embodiments, the web roll may be cut into distinct sections and the sections may be delivered to the converter.

Figure 8:
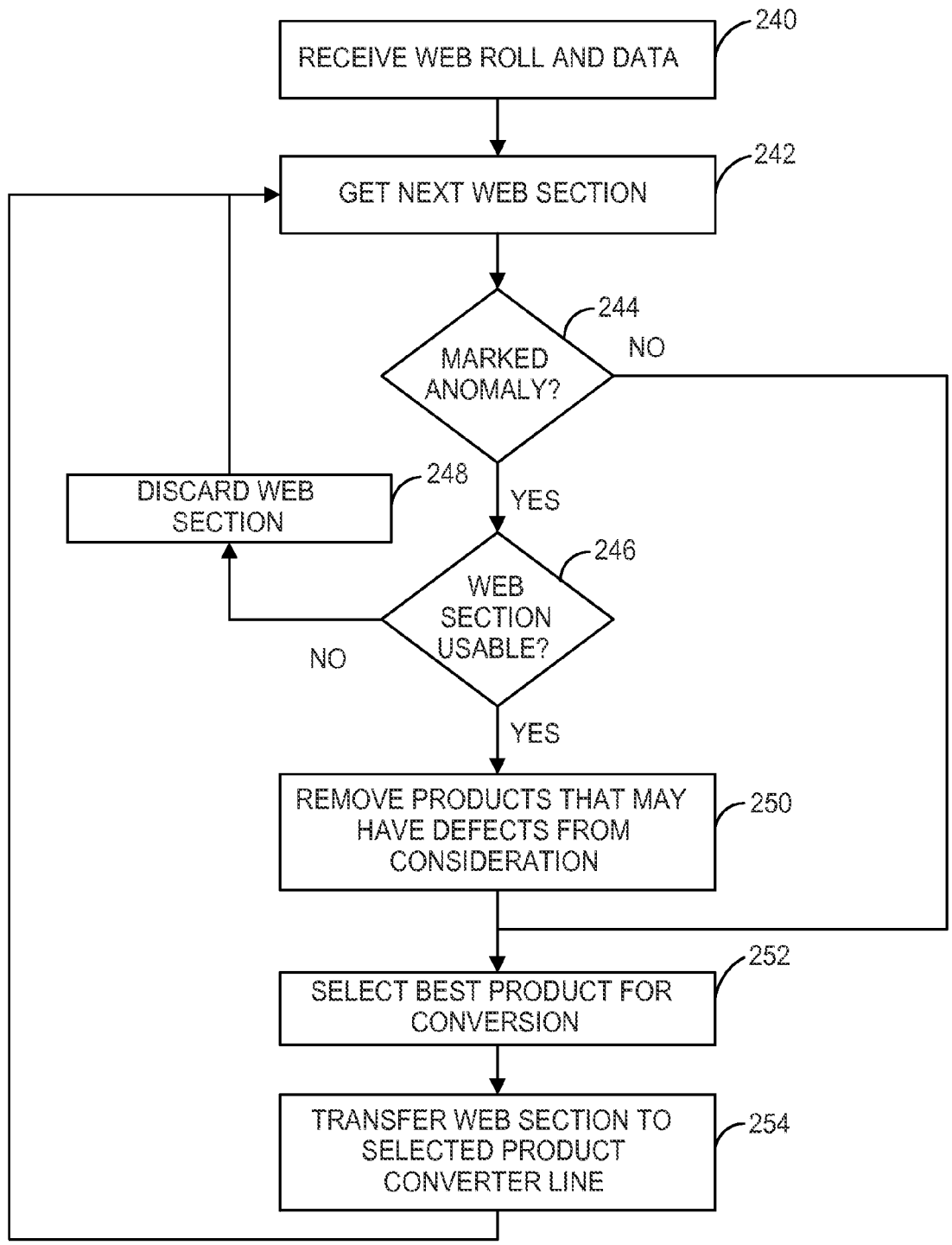
FIG. 8 is a flow chart illustrating an exemplary method of using markings to determine products to assemble from a web.

FIG. 8 is a flow chart illustrating an exemplary method of using the unique markings techniques described herein as an aid to web conversion. First, a converter may receive a finished, marked web roll (240). Additionally, the converter may receive data corresponding to the anomalies in the web roll. The converter may then obtain the first section of the web roll for assembly into products (242). The converter may use a conversion system to automatically perform the task of converting a web roll or web sections into individual sheets for incorporation into products 12, which may include automatically deciding into which of products 12 each sheet should be incorporated. In some embodiments, the converter may load a web roll onto a roller and determine the necessary size of a section of web, then cut the web into the determined-sized sections. In some embodiments, the converter may receive the web already cut into large sections. In still other embodiments, the converter may use the presence or absence of markings on a web to determine the size of a web section.

Once the converter has obtained and loaded a web section, the converter may inspect the web or cover sheet for markings that indicate the presence of an anomaly (244). The converter may use any detection system that is able to detect the presence of the marks as applied by the producer to detect the presence of markings. For example, the converter may use cameras, digital imagers, scanners, laser scanners, or any other suitable system for detecting the presence of markings to indicate the presence of an anomaly.

If an anomaly is present, as indicated by a marking ("YES" branch of 246), the converter may analyze the marking to determine whether there are any products for which the section may be used (248). If not, the section may be discarded or further analyzed to determine whether there may be a product for which the web section may be used that had not previously been considered (248). Otherwise, the products for which the anomaly may cause a defect will be removed from consideration (250). That is, the system may select a product for the web section from among only those products for which the anomaly will not cause a defect.

The converter may utilize any product selection algorithm to select a product for which to convert the web into individual web sections. If a web section has no anomalies ("NO" branch of 246), the entire pool of products for which the web section was intended may be available, otherwise only those products for which the web section will not cause a defect may be available. In any case, the converter may select products for the web according to any selection scheme (252). For example, if the converter may possibly convert web sections into individual sheets for subsequent assembly into three products: products A, B, and C, the converter may prioritize product A as highest priority, B as medium priority, and C as low priority. If a web section can be used for product A, the conversion system will cut the web section into product A. If the web section cannot be used within product A, due to an anomaly that may cause a defect in product A, but can be used within product B, the conversion system will cut the web section as required for subsequent incorporation into product B. If the web section cannot be used within product A or product B but can be used within product C, the conversion system will cut the web section based on the requirements of product C. Otherwise, the conversion system may reject the web section for either disposal or recycling. In some embodiments, the conversion system may select a plurality of products into which a particular web section may ultimately be incorporated. For example, a web section may be most optimally used if the section is converted into a certain number of sheets, some of which may be subsequently assembled into products A and others of which may be assembled into products C. This selection may be based on various factors such as, for example, the size of the section and the sizes of the products, the quality of the section and the qualities required by the various products, or other selection criteria.

As another example, a converter may desire a specific number or distribution for each of products A, B, and C. For example, the converter may want 1,000 units of A, 750 units of B, and 300 units of C. Or, as another example, the converter may want 50% of all production to be product A, 30% to be product B, and 20% to be product C. In either case, the conversion system may be designed to meet these targets. Those skilled in the art will recognize that other selection schemes exist and a converter may use a system that meets other selection schemes without departing from the techniques described herein.

Once a product has been selected, the web section may be converted into individual sheets for assembly into the selected product. Conversion may occur at a separate conversion line, so the web sections may be transferred to the conversion lines associated with the selected product (254). In another embodiment, the conversion lines and a selection line may be part of one large system, so the selection line may perform these steps and direct the web sections to the conversion lines for conversion into individual sheets that may then be assembled into products.

Although discussed with respect to specific embodiments, those having skill in the art will recognize other embodiments that do not depart from the techniques described herein. Therefore the claims should not be limited to those specific embodiments described herein. For example, although many embodiments are described with respect to making a mark to indicate those products for which an anomaly may cause a defect, in another embodiment, the system may make a mark to indicate which products may safely be manufactured from the anomalous region of the web.

Various embodiments of the invention have been described. These and other embodiments are within the scope of the following claims.

The invention claimed is:

1. A method comprising:
obtaining a web to be converted into individual sheets of a plurality of different grade levels;
associating a unique mark with each of the different grade levels;
obtaining anomaly data that identifies positions of anomalies on the web for each of the grade levels, wherein each of the anomalies represents a physical deviation of the web that is a potential defect for at least one of the plurality of different grade levels; and
marking the position of each anomaly on the web at the position of the anomaly, wherein each anomaly is marked with each of the marks corresponding to each of the grade levels for which the anomaly is determined to be a defect.

2. The method of claim 1, wherein marking the position of each anomaly comprises:
applying at least two different application-specific defect detection algorithms to determine that the first one of the anomalies is a defect for at least two of the different plurality of grade levels; and
marking at least two different unique marks on the web at the position for the first one of the anomalies.

3. The method of claim 2, wherein the two different application-specific defect detection algorithms determine that the first one of the anomalies is a defect for the two different plurality of grade levels based on a severity of the physical deviation of the web represented by the first one of the anomalies.

4. The method of claim 3, further comprising applying a third application-specific defect detection algorithm to determine, based on the severity, that the physical deviation of the first one of the anomalies is not a defect for at least one of the plurality of grade levels.

5. The method of claim 1, further comprising:
processing image data of the web to produce the anomaly data to include a plurality of anomaly objects, each of the anomaly objects representing a distinct area of the web and defining a plurality of characteristics for the physical deviation of the web at that distinct area, and
applying a plurality of different application-specific defect detection algorithms to each of the anomaly objects to determine whether each of the anomaly objects represents a defect for each of the different grade levels.

6. The method of claim 5, wherein the characteristics defined by the anomaly objects include a length and a width of the area of the web for the physical deviation.

7. The method of claim 1, wherein marking the position of each anomaly comprises:
applying at least different two different application-specific defect detection algorithms to determine that the first one of the anomalies is a defect for less than all of the different plurality of products; and
marking less than all of the different unique marks on the web at the position for the first one of the anomalies.

8. The method of claim 1, wherein obtaining a web comprises receiving the web from a web producer.

9. The method of claim 1, wherein obtaining a web comprises manufacturing the web as a continuous web.

10. The method of claim 1, wherein obtaining anomaly data comprises receiving the anomaly data from a web producer.

11. The method of claim 1, wherein obtaining anomaly data comprises:
an optical inspection system inspecting the web as the web is produced by a manufacturing line;
an analysis computer locating a position of at least one anomaly that is a potential defect for at least one of the different products into which the web may be converted; and
recording the position of the anomaly.

12. The method of claim 11, further comprising recording each of the products for which the located anomaly is a potential defect along with the recorded position of the anomaly.

13. The method of claim 1, wherein marking the position comprises:
manufacturing the web to include a cover sheet over the web; and
marking each anomaly on the cover sheet at a position that corresponds to the position of the anomaly on the web.

14. The method of claim 1, wherein associating a unique mark comprises associating a unique geometric shape with each of the products.

15. The method of claim 1, wherein associating a unique mark comprises associating a unique color with each of the products.

16. The method of claim 1, wherein associating a unique mark comprises associating a unique number of hash marks with each of the products.

17. The method of claim 1, further comprising transferring the web and the cover sheet to a converter.

18. The method of claim 17, further comprising:
selecting products into which to convert the web in accordance with the marked anomalies; and
converting the web into the selected products.

19. A method comprising:
receiving a web to be converted into individual sheets of a plurality of different grade levels, wherein the web has marks to indicate positions of anomalies on the web, wherein the marks include a unique mark for each of the different grade levels;
separating the web into the individual sheets;
selecting, for each individual sheet, one or more of the products into which to incorporate the sheet in accordance with the marks; and
incorporating each sheet into the selected product or products.

20. The method of claim 19, wherein receiving a web comprises receiving a web covered with a cover sheet, wherein the cover sheet bears the marks to indicate positions of the anomalies on the web.

21. The method of claim 20, further comprising removing the cover sheet from the section before incorporating the sheet into the selected product or products.

22. The method of claim 19, wherein selecting comprises:
inspecting at least one mark to determine in which of the products the anomaly may cause a defect; and
selecting at least one of the products for the sheet bearing the inspected mark for which the anomaly will not cause a defect.

23. A system comprising:
a web of material to be converted into individual sheets of a plurality of different grade levels;
a database storing anomaly data of anomalies on the web, wherein an anomaly is a potential defect in at least one of the plurality of different grade levels;
a marker that associates a unique mark with at least one of the grade levels; and
a controller to retrieve the anomaly data from the database and to signal the marker as to where to make a mark,
wherein the marker applies the mark associated with at least one of the grade levels for which the anomaly is determined to be a defect.

24. The system of claim 23,
wherein the web comprises a cover sheet to cover the web, and
wherein the marker applies the mark to the cover sheet.

25. The system of claim 23, further comprising a plurality of controllers and a plurality of markers, wherein there is one controller for each marker, and wherein there is one marker for each of the grade levels into which the web may be converted.

26. The system of claim 23, further comprising an inspection system to inspect the web, to store the anomaly data in the database, and to determine in which of the products each anomaly may cause a defect.

27. A non-transitory computer-readable medium comprising instructions stored therein for causing a programmable processor to perform:
retrieving web identifying information, wherein the web is to be converted into individual sheets of a plurality of different grade levels;
associating a unique mark with each of the grade levels;
obtaining anomaly data that identifies positions of anomalies on the web for each of the grade levels, wherein each of the anomalies represents a physical deviation of the web that is a potential defect for at least one of the plurality of different grade levels; and
signaling a marker to mark the position of each anomaly on the web at the position of the anomaly, wherein each anomaly is marked with each of the marks corresponding to each of the grade levels for which the anomaly is determined to be a defect.

* * * * *